(12) United States Patent
Miyairi

(10) Patent No.: US 6,367,321 B1
(45) Date of Patent: Apr. 9, 2002

(54) TEST METHOD ON THE STRENGTH OF CERAMIC ENGINE-VALVES AND TESTING DEVICE FOR THE SAME

(75) Inventor: Yukio Miyairi, Nagoya (JP)

(73) Assignee: NGK Insulators, Ltd. (JP)

( * ) Notice: Subject to any disclaimer, the term of this patent is extended or adjusted under 35 U.S.C. 154(b) by 0 days.

(21) Appl. No.: 09/488,517

(22) Filed: Jan. 21, 2000

(30) Foreign Application Priority Data

Feb. 1, 1999 (JP) ............................................. 11-024126

(51) Int. Cl.⁷ ............................................. G02M 15/00
(52) U.S. Cl. ..................................................... 73/119 R
(58) Field of Search ................................ 73/119 R, 116

(56) References Cited

FOREIGN PATENT DOCUMENTS

| JP | 03013842 A | 1/1991 | | |
|---|---|---|---|---|
| JP | 03 013842 | 1/1991 | | |
| JP | 03013842 | * | 1/1992 | ............ G01N/3/08 |
| JP | 05 312678 | 11/1993 | | |
| JP | 0 660 101 | 6/1995 | | |
| JP | 08 043285 | 2/1996 | | |
| JP | 197 05 412 | 8/1998 | | |
| JP | 11 030567 | 2/1999 | | |
| JP | 11030567 A | 2/1999 | | |
| JP | 11064199 A | 3/1999 | | |
| JP | 11 064199 | 3/1999 | | |

OTHER PUBLICATIONS

The abstract labeles XS 0030064510 MA was used in the rejection but there was no date or publisher to match with this prior art that was submitted by applicant.*

* cited by examiner

Primary Examiner—Benjamin R. Fuller
Assistant Examiner—Maurice Stevens
(74) Attorney, Agent, or Firm—Parkhurst & Wendel, L.L.P.

(57) ABSTRACT

A method for testing the strength of a ceramic engine-valve is provided, in which the strength can be tested without producing unnecessary stress in portions other than the places to be tested and without variations in the applied stress during testing; a long time is not taken to set the valve on the testing device while the valve face of the head portion and so forth cannot be damaged during setting. The strength of a cotter-fastening portion of the ceramic engine-valve is tested by fastening and holding only the cotter-fastening portion to one end portion of a main spindle connected to a rotational driving system coaxially with the main spindle; rotatably holding a stem portion at a position separated from the fastening-holding portion by a predetermined span; and applying a load in a direction perpendicular to the stem portion axis at the position on the stem portion separated from the fastening-holding portion by the predetermined span while the valve is rotated about the axial line thereof by rotating the main spindle.

4 Claims, 4 Drawing Sheets

TEST METHOD ON THE STRENGTH OF CERAMIC ENGINE-VALVES AND TESTING DEVICE FOR THE SAME

BACKGROUND OF THE INVENTION

1. Field of the Invention

The present invention relates to a method for testing the strength of ceramic engine-valves and a testing device for the same.

2. Description of the Related Art

A valve for an engine is exposed to high temperature combustion gas and exhaust gas in a cylinder and has to tolerate the internal pressure, the inertial force, and the impactive force in the cylinder as well, so that heat resisting alloys have been conventionally used for forming it. Recently, ceramic such as nitriding silicon that is lighter in weight and more excellent in heat resistance than the heat resisting alloy is tried to use for forming the valves instead of heat resisting alloys. The engine-valve is a reciprocating part at the high speed; when it is made lighter by forming it of the ceramic, it has advantages such as decrease in mechanical failures, improving in engine revolutions, and reduction in engine noises.

However, ceramic has poor ductility compared with metals and when excessive stress is applied to a region of minute defects, a crack originated from the defect is expanded to destruction. Since the lager the defect is, the larger the localized concentrated stress at end portions of the defect is produced, the allowable defect size becomes smaller in the portion to which the larger the stress is applied.

As for the portion to which a small stress is applied, it is possible to guarantee the reliability in the strength of the valve by confirming no large defect by means of a non-destructive defect test such as ultrasonic flaw detection and a penetrating X-ray method; however the non-destructive defect test is insufficient for small defect sizes in portions to which a large stress is applied such as a cotter-groove portion disposed in the vicinity of the end portion of a stem portion and a cotter-fastening portion fastened by a cotter disposed closer to a head portion than the cotter-groove portion because the allowable defect size is small therein.

Therefore, as for the portion to which a large stress is applied as described above, the so-called proof test confirming that no destruction occurs under a predetermined stress by practical carrying out of a load test to produce the predetermined stress in the portion is proposed as a substitution for the non-destructive defect test.

As the proof test, a method such as a tensile test that a cotter is fitted to the stem portion just like in the practical use to apply axial forces to the head portion and the cotter in directions opposite each other and a method (a rotating bending test) that the head portion and the end portion of the stem portion are rotatably held by holding jigs so as to apply a load in a direction roughly perpendicular to the stem portion while rotating the valve is proposed (see Japanese Unexamined Patent Publication No. 3-13842).

However, the tensile test method is improper for inspecting manufactured articles because fitting the parts and setting the valve on the testing device take a long time. The conventional rotating bending test also involves a problem that when a stress is applied to test the cotter-fastening portion to which the maximum stress is practically applied, the same amount of stress or more is produced in the cotter-groove portion to carry out an excessive test relative to the cotter-groove portion after all.

In the rotating bending test, inserting the end portion of the stem portion into the holding jig is the only method for holding it; the amount of clearance between the holding jig and the stem portion is needed; the stem portion is inclined in the holding jig because the holding span is short, producing variations in the stress applied during rotation. Furthermore, in the rotating bending test, the head portion is held by screws, etc., for setting it in the testing device, so that a long time is needed and there is a danger of damaging the valve face of the head portion as well.

SUMMARY OF THE INVENTION

In view of these conventional problems, the present invention has been made. Accordingly, it is an object of the present invention to provide a test method on the strength of ceramic engine-valves, in which when the strength of a cotter-fastening portion and a cotter-groove portion of the valve, to which large amounts of stress are applied when the valve is used, are tested (rotating bending test), unnecessary stress is not applied to portions other than these places to be tested; the applied stress is not changed during testing; a long time is not taken to set the valve on a testing device; and the valve face of a head portion cannot be damaged. It is another object of the present invention to provide a strength-testing device enabling to carry out such the test preferably.

In accordance with a first aspect of the present invention, there is provided a method for testing the strength of a ceramic engine-valve (a first method for testing the strength) comprising an umbrella-shaped head portion and a bar-shaped stem portion, the method comprising the steps of: fastening and holding only a cotter-fastening portion to be fastened by a cotter, disposed closer to the head portion than a cotter-groove portion disposed in the vicinity of the end portion of the stem portion for fitting the cotter thereto, to one end portion of a main spindle connected to a rotational driving system coaxially with the main spindle; rotatably holding the stem portion at a position separated from the fastening-holding portion by a predetermined span; and applying a load in a direction perpendicular to the stem portion axis at the position on the stem portion separated from the fastening-holding portion by the predetermined span while the valve is rotated about the axial line thereof by rotating the main spindle so as to test the strength of the cotter-fastening portion.

In accordance with a second aspect of the present invention, there is provided a method for testing the strength of a ceramic engine-valve (a second method for testing the strength) comprising an umbrella-shaped head portion and a bar-shaped stem portion, the method comprising the steps of: fastening and holding only a portion closer to the end portion of the stem portion than a cotter-groove portion for fitting a cotter thereto disposed in the vicinity of the end portion of the stem portion to one end portion of a main spindle connected to a rotational driving system coaxially with the main spindle; rotatably holding the stem portion at a position separated from the fastening-holding portion by a predetermined span; and applying a load in a direction perpendicular to the stem portion axis at the position on the stem portion separated from the fastening-holding portion by the predetermined span while the valve is rotated about the axial line thereof by rotating the main spindle so as to test the strength of the cotter-groove portion.

In accordance with a third aspect of the present invention, there is provided a device for testing the strength of ceramic engine-valves (a first strength-testing device), comprising: a main spindle held rotatably about the axis thereof, one end thereof having a tapered hole and the other end connected to a rotational driving system via a universal joint; and means for applying a load to applying a load in a direction perpendicular to the axis of a stem portion of the ceramic engine-valve while rotatably holding the stem portion which is fastened and held in the vicinity of the end portion of the stem portion by a collet inserted into the tapered hole of said main spindle and an inner collet fitted inside the collet, wherein the collet has a tapered conical surface in the outer periphery thereof corresponding to that of the tapered hole of the main spindle and is also elastically deformable in the inner-diameter-decreasing direction by applying a radial force from the outer periphery thereof, and wherein the inner collet has an inner peripheral shape for contacting and holding only a cotter-fastening portion of the stem portion of the valve and is also elastically deformable in the inner-diameter-decreasing direction by applying a radial force from the outer periphery thereof.

In accordance with a fourth aspect of the present invention, there is provided a device for testing the strength of ceramic engine-valves (a second strength-testing device), comprising: a main spindle held rotatably about the axis thereof, one end thereof having a tapered hole and the other end connected to a rotational driving system via a universal joint; and means for applying a load to apply a load in a direction perpendicular to the axis of a stem portion of the ceramic engine-valve while rotatably holding the stem portion which is fastened and held in the vicinity of the end portion of the stem portion by a collet inserted into the tapered hole of the main spindle and an inner collet fitted inside the collet, wherein the collet has a tapered conical surface in the outer periphery thereof corresponding to that of the tapered hole of the main spindle and is also elastically deformable in the inner-diameter-decreasing direction by applying a radial force from the outer periphery thereof, and wherein the inner collet has an inner peripheral shape for contacting and holding only a portion closer to the end portion of the stem portion than a cotter groove disposed in the stem portion of the valve and is also elastically deformable in the innerdiameter-decreasing direction by applying a radial force from the outer periphery thereof.

DESCRIPTION OF THE PREFERRED EMBODIMENTS

Figure 5:
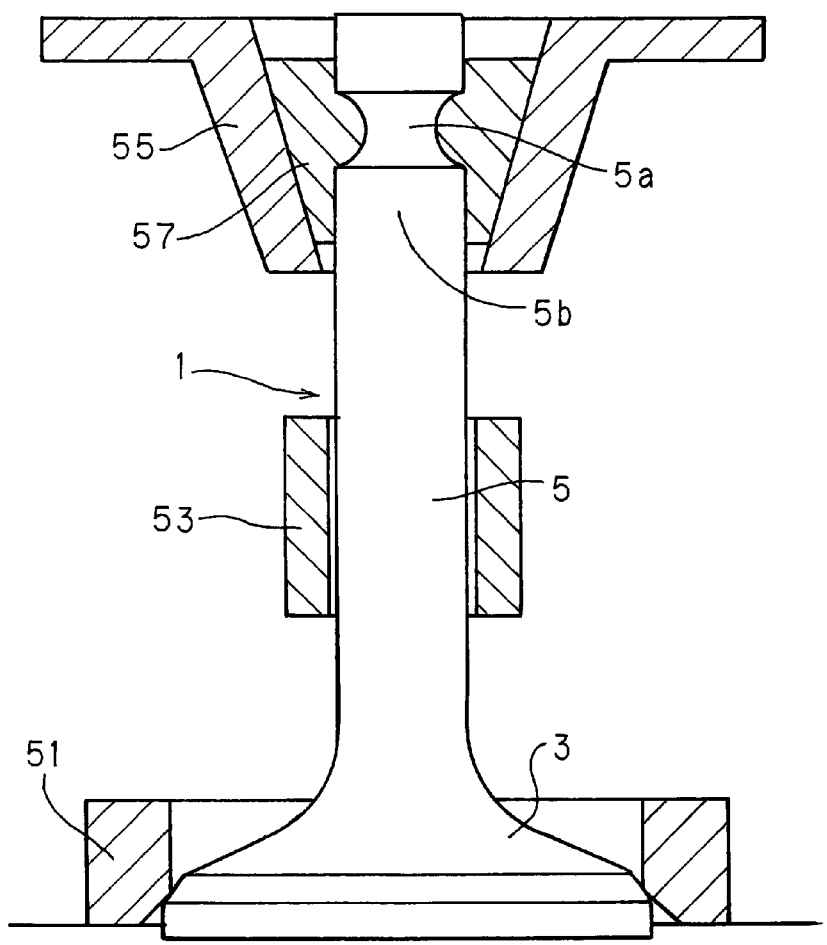
FIG. 5 is a brief drawing of a ceramic engine-valve equipped in an engine.

FIG. 5 is a brief drawing of a ceramic engine-valve equipped in an engine. The ceramic engine-valve 1 comprises an umbrella-shaped head portion 3 touched to a valve sheet 51 and a bar-shaped stem portion 5 supported by a guide 53.

The stem portion 5 includes a cotter-groove portion 5a disposed in the vicinity of the end portion thereof (a stem end) for fitting a cotter 57 to be fitted into a retainer 55. Large amounts of stress are applied to the cotter-groove portion 5a and a cotter-fastening portion 5b disposed in a more downward position than that of the cotter-groove portion 5a (the head portion 3 side) to be fastened by the cotter 57.

A first method for testing the strength according to the present invention is to test the strength of the cotter fastening portion 5b in the two portions to which large amounts of stress are applied. In this method, only the cotter-fastening portion 5b is held by fastening coaxially to one end portion of a main spindle connected to a rotational driving system while a position on the stem portion separated from the fastenin-holdin portion predetermined span is rotatably held, wherein a load is applied to the above-mentioned position on the stem portion separated from the fastening-holding portion by the predetermined span in a direction perpendicular to the stem portion axis while the valve is rotated about the axial line thereof by the rotation of the main spindle.

Figure 1:
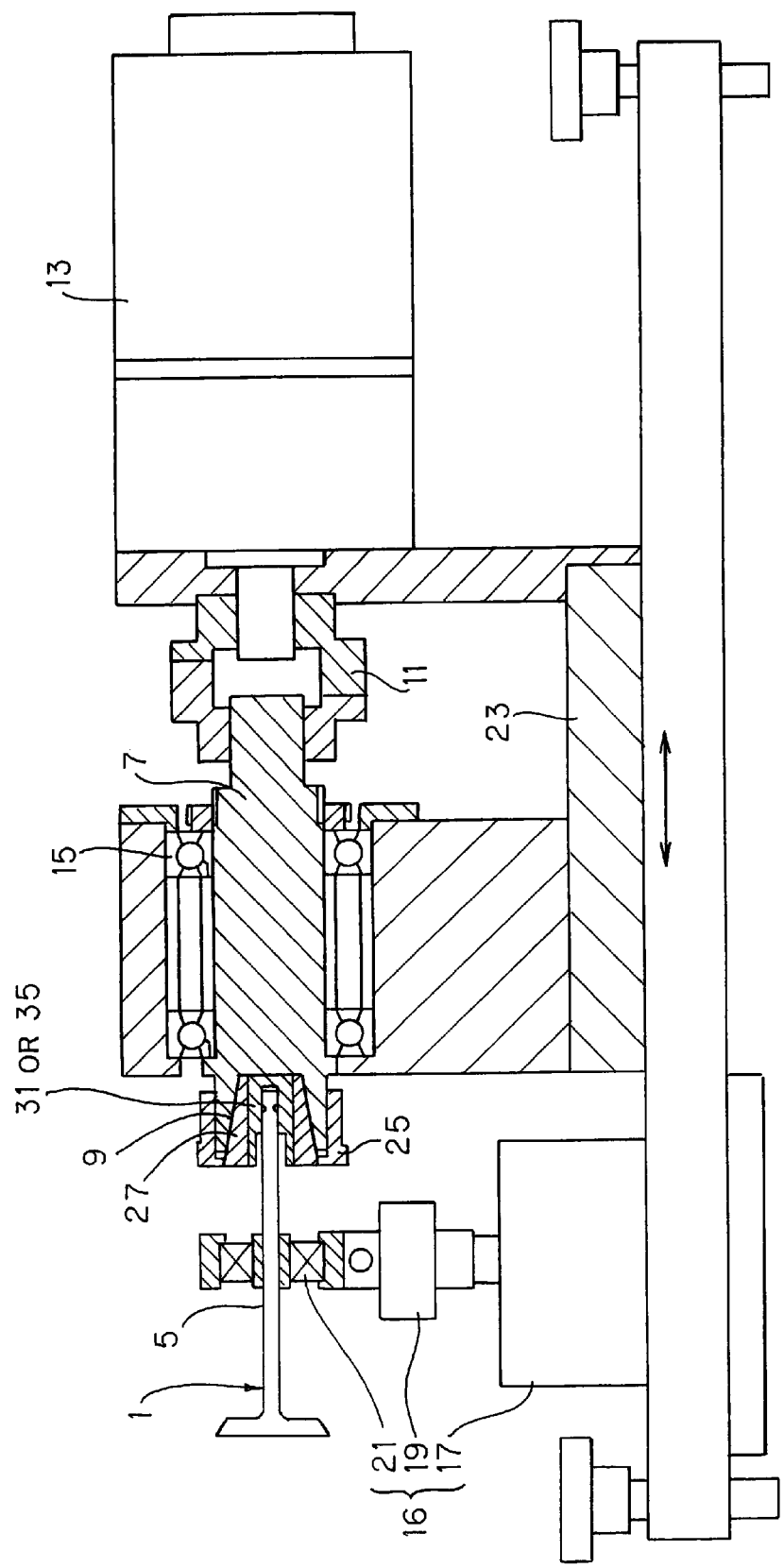
FIG. 1 is a brief drawing of a strength-testing device according to the present invention.

The first method for testing the strength can be carried out using a strength-testing device formed as shown in FIG. 1. This device (a first strength-testing device) comprises a main spindle 7 held rotatably about the axis thereof by bearings 15, etc., having a tapered hole 9 in one end thereof while the other end being connected to the rotational driving system formed of an electrical motor 13, etc., via a universal joint 11. The device comprises means for applying a load 16 to apply a load in a direction perpendicular to the axis of the stem portion 5 while holding the stem portion 5 of a ceramic engine-valve 1 rotatably in which the vicinity of the end portion of the stem portion 5 is fastening by a collet 27 inserted into the tapered hole 9 of the main spindle 7 and an inner collet 31 fitted inside the collet 27.

The means for applying a load 16 is formed of an air cylinder 17, a load cell 19 disposed on the air cylinder 17, and a bearing 21 fixed on the top portion of the load cell 19 for rotatably holding the stem portion 5 of the ceramic engine-valve 1 inserted into the inner peripheral portion of the bearing 21. In the means for applying a load 16, the applying load to the ceramic engine-valve 1 can be controlled by adjusting the air pressure by the pressure adjusting valve for supplying air to the air cylinder 17; the rising up speed of the load can be controlled by adjusting the restriction of the pressure supplying path to the air cylinder 17.

The main spindle 7 and the rotational driving system such as the electrical motor 13 are disposed on a pedestal 23 slidable in the arrow directions in FIG. 1. A load can be applied to an arbitrary position on the stem portion 5 of the ceramic engine-valve 1 held by the main spindle 7 in a direction perpendicular to the axis thereof by adjusting the distance to the means for applying a load 16 by sliding the pedestal 23.

Figure 2:
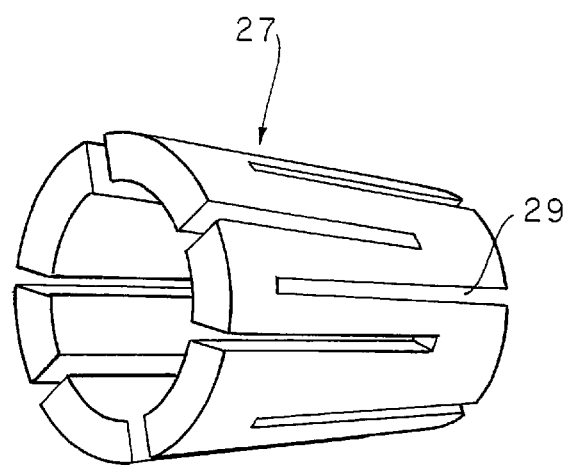
FIG. 2 is a brief perspective view showing the structure of a collet for use as the strength-testing device according to the present invention.

The collet 27 inserted into the tapered hole 9 of the main spindle 7 has the same tapered conical surface in the outer periphery as that of the hole 9. The collet 27 also has a structure in which elastic deformation is possible to occur in the inner-diameter-decreasing direction by applying a radial force from the outer periphery by means of forming slits 29 and so forth as shown in FIG. 2.

Figure 3:
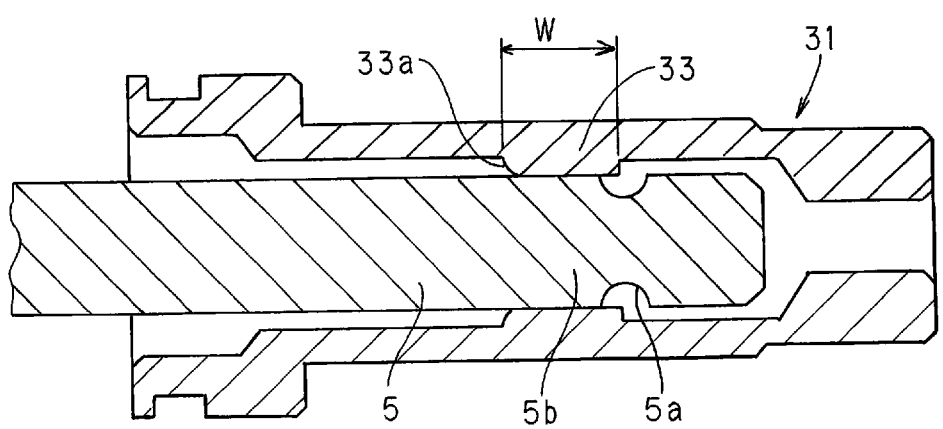
FIG. 3 is a brief sectional view showing an inner collet for use as a strength-testing device (a first strength-testing device) according to the present invention.

The inner collet 31 fitted inside the collet 27 has an inner peripheral shape to contact and hold the cotter fastening portion 5b on the stem portion 5. Specifically, as shown in FIG. 3, the inner collet 31 comprises a fastening-holding portion 33 having a reduced inner diameter and approximately the same width as that of the cotter-fastening portion 5b. On both sides of the fastening-holding portion 33, the inner diameters thereof are larger than the outer diameter of the stem portion 5 when the cotter-fastening portion 5b of the stem portion 5 is held by the fastening-holding portion 33, so that clearances from the stem portion 5 are produced.

In addition, it is preferable that the edge 33a of the fastening-holding portion 33 in the side for inserting the stem portion 5 be R-shaped to thereby enable to prevent the stem portion 5 from generating excessive stress. The inner collet 31 has a structure in which elastic deformation is possible to occur in the inner-diameter-decreasing direction by applying a radial force from the outer periphery by means of forming slits and so forth just like in the above-mentioned collet 27.

Therefore, when this inner collet 31 is fitted inside the collet 27 and the end surface of the collet 27 in the larger diameter side is axially fastened by a screw 25, etc., as shown in FIG. 1, an inwardly radial force is applied to the outer periphery of the collet 27 to deform it elastically in the inner-diameter-reducing direction while an inwardly radial force is also applied to the outer periphery of the inner collet 31 inside the collet 27 to deform it elastically in the inner-diameter-reducing direction, so that the fastening-holding portion 33 fastens only the cotter-fastening portion 5b of the stem portion 5 inserted into the inner collet 31.

In this manner, in the state that only the cotter-fastening portion 5b on the stem portion 5 of the ceramic engine-valve 1 is fastened to the main spindle 7 via the inner collet 31 and the collet 27 while a position on the stem portion 5 separated from the fastening-holding portion thereof by a predetermined span is rotatably held by the bearing 21 of the means for applying a load 16, a load in a direction perpendicular to the axis of the stem portion 5 is applied to the holding position on the stem portion 5 held by the bearing 21 by the means for applying a load 16 while the valve 1 is rotated about the axial line thereof by rotating the main spindle 7 by the rotational driving system.

In the first method for testing the strength, the existence of a defect larger than the allowable defect size on the surface of the cotter-fastening portion 5b over the whole periphery thereof can be tested by rotating the ceramic engine-valve 1 by one or more revolutions while a predetermined load is applied.

In this method for testing the strength, since only the cotter-fastening portion 5b, the strength thereof is to be tested, is held to the main spindle 7 while applying rotation to the ceramic engine-valve 1, unnecessary stresses cannot be produced in portions other than the cotter-fastening portion 5b such as the cotter-groove portion 5a. Furthermore, since the ceramic engine-valve 1 is held to the main spindle 7 by not only simply inserting the valve into the holding jig but also fastening it, applied stress cannot be changed by inclination of the stem portion 5 in the holding jig (the inner collet 31) during rotation of the valve 1. Still furthermore, the head portion 3 of the valve 1 is not held, so that the face of the head portion 3 and so forth cannot be damaged and the valve can be set on the testing device in a short time.

A second method for testing the strength according to the present invention is to test the strength of the cotter-groove portion 5a in the aforementioned two portions to which large amounts of stress are applied. In this method, only a portion 5c, which is closer to the end of the stem portion than the cotter-groove portion 5a, is held by coaxially fastening to one end portion of the main spindle connected to the rotational driving system while a position on a stem portion separated from the fastening-holding portion by a predetermined span is rotatably held, wherein a load is applied at the above-mentioned position separated from the fastening-holding portion by the predetermined span on the stem portion in a direction perpendicular to the stem portion axis while the valve is rotated about the axial line thereof by the rotation of the main spindle.

A device for use as the second method for testing the strength (a second strength-testing device) is basically identically formed to the above-mentioned first strength-testing device shown in FIG. 1; however an inner collet has an inner peripheral shape to contact and hold only the portion 5c, which is closer to the end of the stem portion than the cotter-groove portion 5a disposed on the stem portion 5 of the valve 1.

Figure 4:
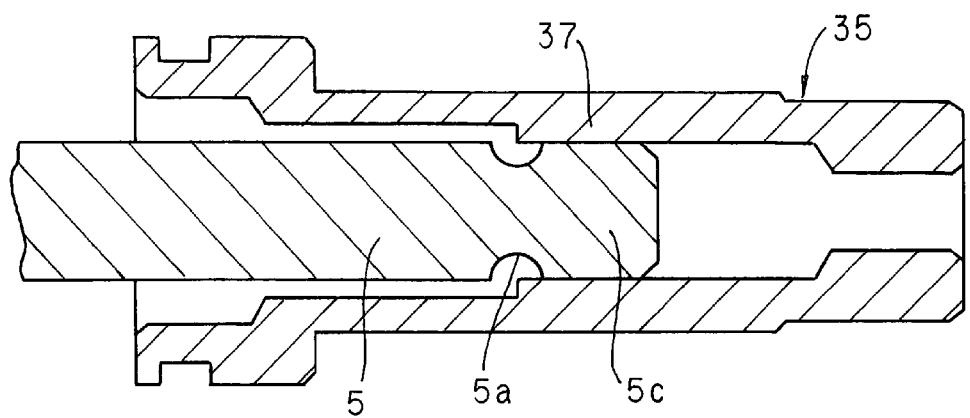
FIG. 4 is a sectional view showing an inner collet for use as a strength-testing device (a second strength-testing device) according to the present invention.

Specifically, as shown in FIG. 4, the inner collet 35 comprises a fastening-holding portion 37 for fastening and holding the portion 5c in a part of the inner periphery thereof closer to the stem portion end than the cotter-groove portion 5a. In portions closer to an opening for inserting the stem portion 5 than the fastening-holding portion 37, the inner diameters thereof are larger than the outer diameter of the stem portion 5 when the portion 5c closer to the stem portion end than the cotter-groove portion 5a is held by the fastening-holding portion 37, so that clearances from the stem portion 5 are produced.

In addition, the inner collet 35 also has a structure in which elastic deformation is possible to occur in the inner-diameter-decreasing direction by applying a radial force from the outer periphery by means of forming slits and so forth just like in the above-mentioned collet 27.

Therefore, when this inner collet 35 is fitted inside the collet 27 and the end surface of the collet 27 in the larger diameter side is axially fastened by the screw 25, etc., as shown in FIG. 1, an inwardly radial force is applied to the outer periphery of the collet 27 to deform it elastically in the inner-diameter-reducing direction while an inwardly radial force is also applied to the outer periphery of the inner collet 35 inside the collet 27 to deform it elastically in the inner-diameter-reducing direction, so that the fastening-holding portion 37 fastens only the portion 5c inserted into the inner collet 35 closer to the stem portion end than the cotter-groove portion 5a on the stem portion 5.

In this manner, in the state that only the portion 5c closer to the stem portion end than the cotter-groove portion 5a of the ceramic engine-valve 1 is fastened to the main spindle 7 via the inner collet 35 and the collet 27 while a position on the stem portion 5 separated from the fastening-holding portion thereof by a predetermined span is rotatably held by the bearing 21 of the means for applying a load 16, a load in a direction perpendicular to the axis of the stem portion 5 is applied to the holding position on the stem portion 5 held by the bearing 21 by the means for applying a load 16 while the valve 1 is rotated about the axial line thereof by rotating the main spindle 7 by the rotational driving system.

In the second method for testing the strength, the existence of a defect larger than the allowable defect size on the surface of the cotter-groove portion 5a over the whole periphery thereof can be tested by rotating the ceramic engine-valve 1 by one or more revolutions while a predetermined load is applied.

In this method for testing the strength, since only the portion 5c closer to the stem portion end than the cotter-groove portion 5a, the strength thereof is to be tested, is held to the main spindle 7 applying rotation to the ceramic engine-valve 1, unnecessary stresses cannot be produced in portions other than the cotter-groove portion 5a.

Furthermore, since the ceramic engine-valve 1 is held to the main spindle 7 by not only simply inserting the valve into the holding jig but also fastening it, applied stress cannot be changed by inclination of the stem portion 5 in the holding jig (the inner collet 35) during rotation of the valve 1. Still furthermore, the head portion 3 of the valve 1 is not held, so that the face of the head portion 3 and so forth cannot be damaged and the valve 1 can be set on the testing device in a short time.

As described above, according to the present invention, when tests (rotating bending tests) are carried out on the strength of the cotter-fastening portion and the cotter-groove portion where large amounts of stress are produced during using of a ceramic engine-valve, the strength can be tested without producing unnecessary stress in portions other than these places to be tested and without variations in the applied stress during testing. A long time is not taken to set the valve on the testing device while the valve face of the head portion and so forth cannot be damaged during setting.

What is claimed is:

1. A method for testing the strength of a ceramic engine-valve comprising an umbrella-shaped head portion at one end and a bar-shaped stem portion which extends to the opposing end of the valve, the end portion of the bar-shaped stem portion having a cotter-groove portion near the end of the end portion and a cotter-fastening portion on the end portion of the stem portion which is closer to the umbrella-shaped head portion than the cotter-groove portion, said method comprising the steps of:

fastening and holding only the cotter-fastening portion to be fastened by a cotter to one end portion of a main spindle connected to a rotational driving system coaxially with the main spindle;

rotatably holding the stem portion at a position separated from the cotter-fastening portion being held by a predetermined span; and applying a load in a direction perpendicular to the stem portion axis at the position on the stem portion separated from the cotter-fastening portion being held by the predetermined span while the valve is rotated about the axial line thereof by rotating the main spindle so as to test the strength of the cotter-fastening portion.

2. A method for testing the strength of a ceramic engine-valve comprising an umbrella-shaped head portion at one end and a bar-shaped stem portion which extends to the opposing end of the valve, the end portion of the bar-shaped stem portion having a cotter-groove portion near the end of the end portion and a cotter-fastening portion on the end portion of the stem portion which is closer to the umbrella-shaped head portion than the cotter-groove portion, said method comprising the steps of:

fastening and holding only a portion closer to the end portion of the stem portion than the cotter-groove portion for fitting a cotter thereto to one end portion of a main spindle connected to a rotational driving system coaxially with the main spindle;

rotatably holding the stem portion at a position separated from the portion closer to the end portion of the stem portion than the cotter-groove portion which is being held by a predetermined span; and applying a load in a direction perpendicular to the stem portion axis at the position on the stem portion separated from the portion closer to the end portion of the stem portion than the cotter-groove portion which is being held by the predetermined span while said valve is rotated about the axial line thereof by rotating the main spindle so as to test the strength of the cotter-groove portion.

3. A device for testing the strength of a ceramic engine-valve having an umbrella-shaped head portion at one end and a bar-shaped stem portion which extends to the opposing end of the valve, the end portion of the bar-shaped stem portion having a cotter-groove portion near the end of the end portion and a cotter-fastening portion on the end portion of the stem portion which is closer to the umbrella-shaped head portion than the cotter-groove portion, comprising:

a main spindle having an axis, two ends and held rotatably about the axis thereof, one end thereof having a tapered hole and the other end connected to a rotational driving system by means of a universal joint; and means for applying a load to apply a load in a direction perpendicular to the axis of a stem portion of said ceramic engine-valve while rotatably holding the cotter-fastening portion by a collet inserted into the tapered hole of said main spindle and an inner collet fitted inside the collet, wherein the collet has a tapered conical surface in the outer periphery thereof corresponding to that of the tapered hole of said main spindle and wherein the collet has an inner peripheral shape with an internal diameter which is elastically deformable so as to decrease the internal diameter by applying a radial force from the outer periphery thereof, and wherein the inner collet has a surface in the outer periphery thereof for engagement with the inner peripheral shape of the collet and an inner peripheral shape for contacting and holding only a cotter-fastening portion on the stem portion of said valve and wherein the inner collet has an inner peripheral shape with an internal diameter which is elastically deformable so as to decrease the internal diameter by applying a radial force from the outer periphery thereof.

4. A device for testing the strength of ceramic engine-valve having an umbrella-shaped head portion at one end and a bar-shaped stem portion which extends to the opposing end of the valve, the end portion of the bar-shaped stem portion having a cotter-groove portion near the end of the end portion and a cotter-fastening portion on the end portion of the stem portion which is closer to the umbrella-shaped head portion than the cotter-groove portion, comprising:

a main spindle having an axis, two ends and held rotatably about the axis thereof, one end thereof having a tapered hole and the other end connected to a rotational driving system by means of a universal joint; and means for applying a load to apply a load in a direction perpendicular to the axis of a stem portion of said ceramic engine-valve while rotatably holding a stem portion closer to the end portion of the stem portion than the cotter-groove portion by a collet inserted into the tapered hole of said main spindle and an inner collet fitted inside the collet, wherein the collet has a tapered conical surface in the outer periphery thereof corresponding to that of the tapered hole of said main spindle and wherein the collet has an inner peripheral shape with an internal diameter which is elastically deformable so as to decrease the internal diameter by applying a radial force from the outer periphery thereof, and wherein the inner collet has a surface in the outer periphery thereof for engagement with the inner peripheral shape of the collet and an inner peripheral shape for contacting and holding only the stem portion closer to the end portion of the stem portion than the cotter-groove portion and wherein the inner collet has an inner peripheral shape with an internal diameter which is also elastically deformable so as to decrease the internal diameter by applying a radial force from the outer periphery thereof.

* * * * *